United States Patent [19]

Schoolman

[11] Patent Number: 4,737,972
[45] Date of Patent: Apr. 12, 1988

[54] STEREOSCOPIC FLUOROSCOPE ARRANGEMENT

[76] Inventor: Arnold Schoolman, 6420 Prospect, Kansas City, Mo. 64132

[21] Appl. No.: 935,066

[22] Filed: Nov. 21, 1986

Related U.S. Application Data

[63] Continuation of Ser. No. 671,436, Nov. 14, 1984, abandoned, which is a continuation-in-part of Ser. No. 616,385, Jun. 1, 1984, Pat. No. 4,559,555, which is a continuation-in-part of Ser. No. 351,917, Feb. 24, 1982, abandoned.

[51] Int. Cl.[4] ............... A61B 6/03; H05G 1/64; H04N 5/32
[52] U.S. Cl. ............... 378/41; 378/42; 378/99; 358/111
[58] Field of Search ............... 378/99, 41, 42; 358/111

[56] References Cited

U.S. PATENT DOCUMENTS

| | | | |
|---|---|---|---|
| 2,995,156 | 10/1960 | Heilig | 358/88 |
| 3,670,097 | 6/1972 | Jones | 358/91 |
| 3,883,689 | 5/1975 | Mansour et al. | 358/227 |
| 3,919,475 | 11/1975 | Dukich et al. | 358/210 |
| 3,923,370 | 12/1975 | Mostrom | 350/294 |
| 3,940,204 | 2/1976 | Withrington | 350/3.72 |
| 3,976,840 | 8/1976 | Cleveland et al. | 364/900 |
| 4,028,725 | 6/1977 | Lewis | 358/103 |
| 4,034,401 | 7/1977 | Mann | 358/93 |
| 4,051,802 | 9/1977 | Dukich et al. | 358/210 |
| 4,115,802 | 9/1978 | Kramer et al. | 358/93 |
| 4,153,913 | 5/1979 | Swift | 358/93 |
| 4,160,263 | 7/1979 | Christy et al. | 358/1 |
| 4,214,267 | 7/1980 | Roese et al. | 378/42 |
| 4,242,703 | 12/1980 | Tsukoshima et al. | 358/150 |
| 4,246,607 | 1/1981 | Vijverberg | 358/111 |
| 4,247,908 | 1/1981 | Lockhart, Jr. et al. | 364/900 |
| 4,266,271 | 5/1981 | Chamoff et al. | 364/200 |
| 4,277,837 | 7/1981 | Stuckert | 364/900 |
| 4,310,849 | 1/1982 | Glass | 358/88 |
| 4,345,315 | 8/1982 | Cadotte et al. | 364/900 |
| 4,360,875 | 11/1982 | Behnke | 364/900 |
| 4,395,731 | 7/1983 | Schoolman | 358/88 |
| 4,398,799 | 8/1983 | Swift | 350/174 |
| 4,434,500 | 2/1984 | Lemke | 378/99 |
| 4,447,827 | 5/1984 | Alexandreseu et al. | 358/111 |
| 4,449,195 | 5/1984 | Andrews et al. | 364/900 |

OTHER PUBLICATIONS

Aviation Week & Space Technology, Oct. 11, 1983, p. 133 (Visnad Device).
An Introduction to the Physics of Diagnostic Radiology, E. E. Christensen et al. 2nd ed., 1978, Ch. 19, pp. 276-277.

*Primary Examiner*—Carolyn E. Fields
*Assistant Examiner*—Joseph A. Hynds
*Attorney, Agent, or Firm*—Litman McMahon & Brown

[57] ABSTRACT

A stereoscopic fluoroscope apparatus includes a pair of spaced x-ray tubes mounted on a support opposite a respective pair of x-ray image intensifiers having a pair of video cameras coupled thereto. The x-ray tubes and image intensifiers are positioned to form a stereoscopic pair of fluorescent images which are converted to video signals by the cameras. The cameras are connected to a head worn video stereoscopic display including miniature right and left video display devices therein for stereoscopic viewing of the images produced by irradiating a target of examination. The apparatus includes provisions for selectively routing the video signals representing the x-ray images to external signal receivers such as remote video monitors, video recorders, or computers and for routing external video signals to the stereoscopic display unit for displaying the images represented thereby.

16 Claims, 3 Drawing Sheets

STEREOSCOPIC FLUOROSCOPE ARRANGEMENT

CROSS-REFERENCE TO RELATED APPLICATIONS

The present invention is a continuation of U.S. patent application Ser. No. 671,436 filed Nov. 14, 1984, abandoned, which was a continuation-in-part of U.S. patent application Ser. No. 616,385 for STEREOSCOPIC REMOTE VIEWING SYSTEM filed June 1, 1984 and now U.S. Pat. No. 4,559,555 which was a Continuation-in-Part of U.S. patent application Ser. No. 351,917 for PORTABLE REMOTE TERMINAL WITH HEAD HELD DISPLAY, filed Feb. 24, 1982, now abandoned.

FIELD OF THE INVENTION

The present invention relates to fluoroscopy and, more particularly, to a stereoscopic fluoroscope apparatus wherein the images are displayed on video display devices within a head worn video stereoscopic display unit.

BACKGROUND OF THE INVENTION

Stereoscopy was introduced to radiology in 1898, and by 1930, most radiographs were taken stereoscopically. The technique used principally in early methods was to place a photographic plate behind the patient, take an exposure, replace the plate, shift the x-ray tube laterally, and take a second exposure. The developed films were then viewed in a stereoscopic viewer apparatus. The additional expense and exposure, with the discovery that overexposure to x-rays is harmful, led to the decline of stereoscopic x-ray techniques.

In order to reduce patient exposure by x-rays, intensifying and fluoroscopic screens were developed. Intensifying screens are fluorescent screens which emit light when the phosphors thereof are excited by x-rays. The light emitted exposes a photographic emulsion. In fluoroscopy, the fluorescent screen is viewed directly. Patient exposure is reduced by these methods several hundredfold.

One of the problems with early fluoroscopy was that the fluorescent screens were too dim for daylight (photopic) vision which is sharper than night (scotopic) vision. To overcome this problem, x-ray image intensifiers were developed. In an image intensifier, an input fluorescent screen absorbs x-ray photons and converts their energy into light photons. The light photons strike a photocathode causing it to emit photoelectrons which are drawn away by the high potential of an accelerating anode. An electrostatic lens focuses the electrons onto an output fluorescent screen which emits light which is viewed by the observer. Image intensifiers are often coupled with motion picture, television, or spot film cameras for recording the output fluorescent images.

SUMMARY OF THE INVENTION

The present invention resolves certain problems associated with early stereoscopic x-ray methods. A pair of x-ray tubes irradiate a corresponding pair of x-ray image intensifiers through a target of examination, and the fluorescent images are converted to video signals which are displayed on video display devices of a video stereoscopic display unit which is preferably worn on the head of the observer. A timer switch is connected to the x-ray tubes and alternately activates the x-ray tubes in rapid succession such that the target is only illuminated by one x-ray source at a time.

OBJECTS OF THE INVENTION

The principal objects of the present invention are: to provide an improved fluoroscopic examination apparatus; to provide a stereoscopic fluoroscope apparatus for stereoscopic viewing of x-ray irradiated targets; to provide such an apparatus including a pair of spaced apart x-ray tubes, a pair of x-ray image intensifiers each having a video camera coupled thereto, a timer switch to alternately activate the x-ray tubes, and a video stereoscopic display unit including a pair of video display devices positioned for stereoscopic viewing of images displayed thereon; to provide such an apparatus wherein the video signals can be displayed monoscopically on remote video monitors; to provide such an apparatus wherein the video signals can be recorded by a video recorder and wherein previously recorded video signals can be displayed on the display unit; to provide such an apparatus wherein the video signals can be digitized and stored or computer enhanced and the enhanced images displayed on the display unit; to provide such an apparatus which is adaptable to industrial and security applications as well as medical uses; and to provide such a stereoscopic fluoroscope apparatus which is economical to manufacture, precise in use, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE PREFERRED EMBODIMENTS

Figure 1:
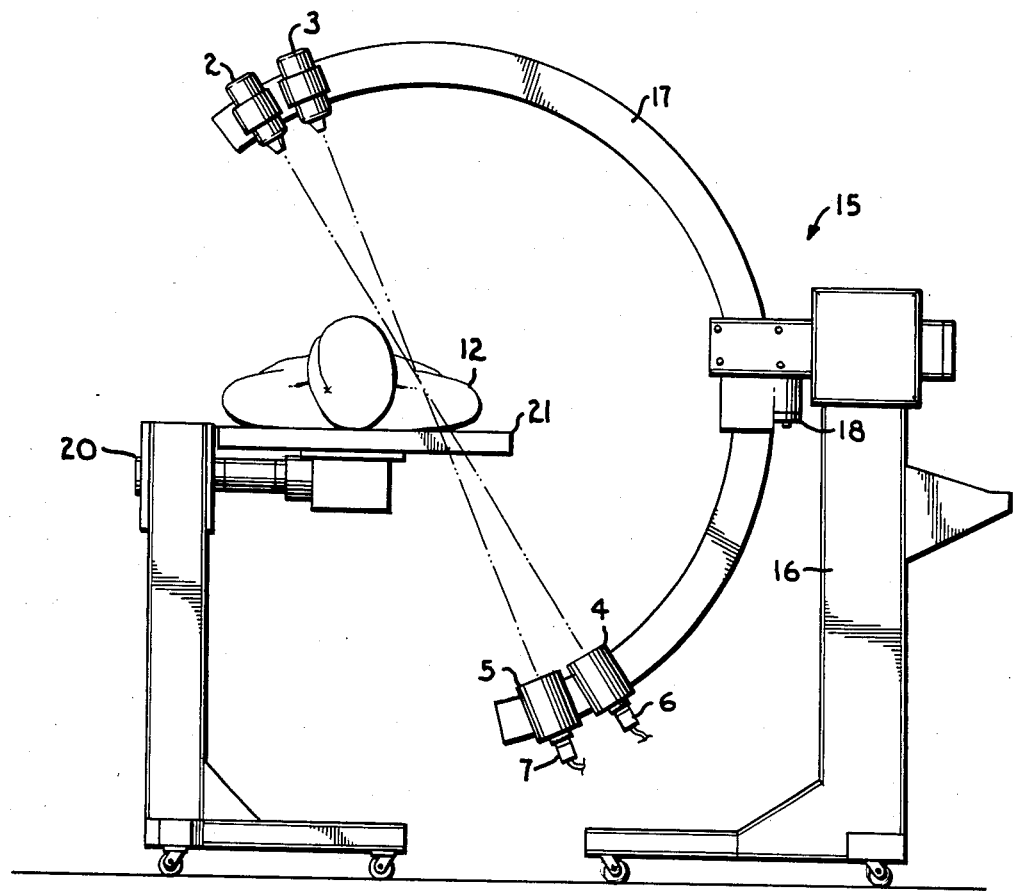
FIG. 1 is an elevational view of a support arm mounting the x-ray tubes, image intensifiers, and video cameras of the steroscopic fluoroscope apparatus according to the present invention.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates a stereoscopic fluoroscope apparatus (FIG. 2) according to the present invention. The apparatus 1 generally includes a right x-ray source or tube 2, a left x-ray source or tube 3, respective right and left x-ray image intensifiers 4 and 5 positioned to receive the x-rays from the associated tubes, respective right and left video cameras 6 and 7 optically coupled to the image intensifiers to convert the fluorescent images thereof to video signals, and a video stereoscopic display unit 8 housing right and left video display devices 9 and 10 for displaying the images represented by the video signals. An x-ray source timer switch 11 periodically activates the x-ray tubes 2 and 3 and the video cameras associated therewith in alternation whereby a target of examination 12 (FIG. 1) is irradiated by a single x-ray tube at a time.

FIG. 1 illustrates an exemplary support structure 15 on which the x-ray tubes 2 and 3, the image intensifiers 4 and 5, and the video cameras 6 and 7 are mounted. The structure 15 includes a support base 16 having a support arm 17 connected thereto. The illustrated support arm 17 is semicircular and is slidably mounted on the base 16. A motor 18 is mounted on the base 16 and mechanically engages the periphery the arm 17 such that rotation of the motor 18 drives and revolves the arm 17 about its circular axis. The motor 18 preferably has a worm gear (not shown) on its shaft which meshes with gear teeth (not shown) on the periphery of the arm 17. The support structure 15 may incorporate provisions for raising and lowering the entire arm 17 (not shown).

The x-ray tube pair and the image intensifier pair are mounted in diametric opposition on the arm with the target 12 therebetween. As illustrated, the respective positions of the tubes 2 and 3 and intensifiers 4 and 5 are fixed relative to the support arm 17. However, there is no inherent requirement for this. In other embodiments, the x-ray tubes and image intensifiers could be movable with respect to their support member and each other. The lines of sight between the x-ray tubes 2 and 3 and their respective image intensifiers 4 and 5 mutually intersect, preferably within the target 12 to thereby form image pairs which are distinct enough to provide a three dimensional view of the target but not so diverse as to prevent stereoscopic registration of the images by a viewer.

The target 12 illustrated in FIG. 1 is a human patient positioned on a platform 20. The platform 20 is preferably adjustable to precisely position the patient in relation to the support structure 15. The platform 20 includes a patient support 21 which is radiotransparent, that is, which does not substantially absorb, reflect, or otherwise interfere with the x-rays from the tubes 2 and 3. While the stereoscopic fluoroscope arrangement 1 is illustrated in a medical environment, the invention is not limited to such an application and would provide advantages over conventional monoscopic fluoroscopes in industrial fluoroscopy, in security applications such as carry-on luggage inspections at airports, and other fields.

Figure 2:
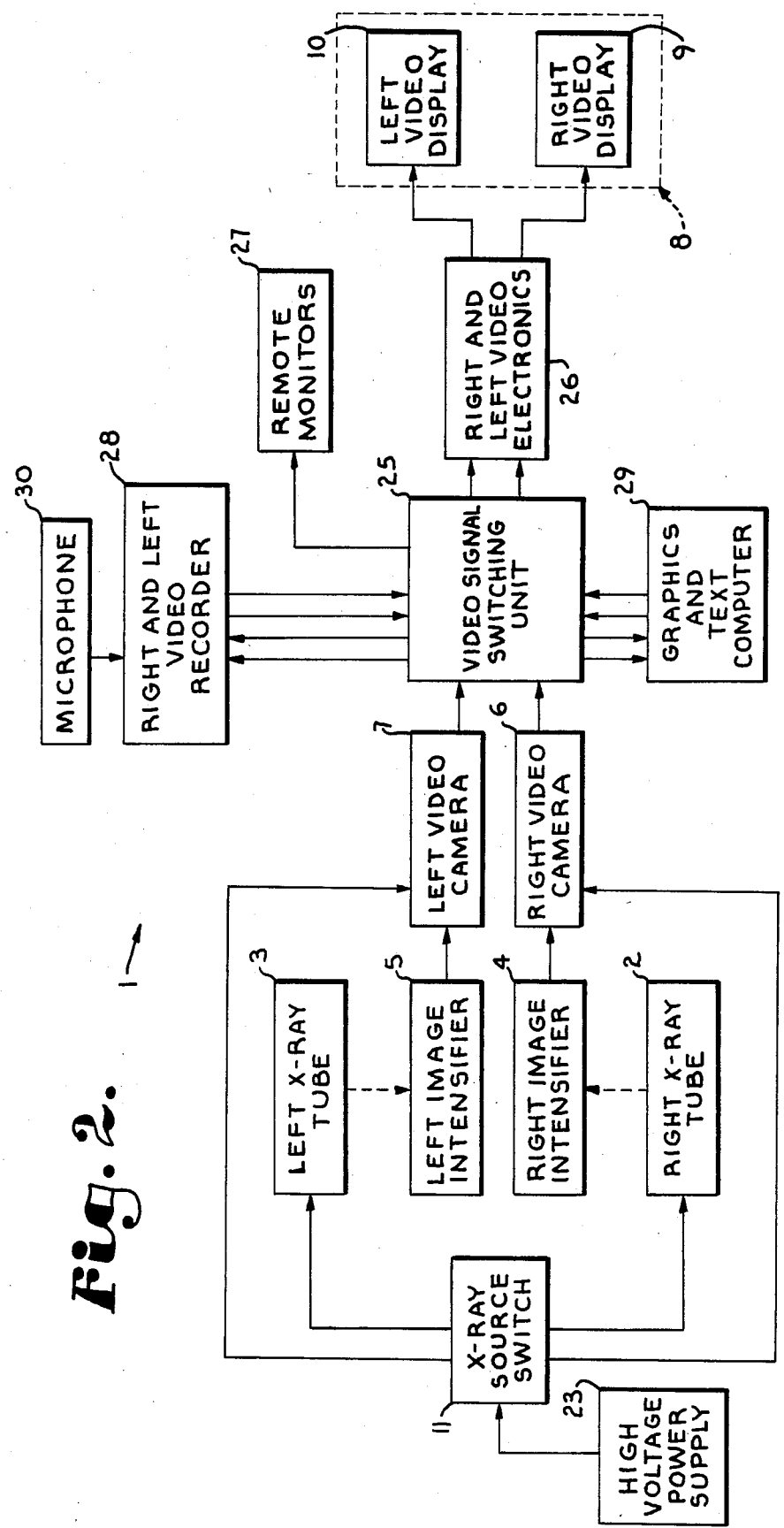
FIG. 2 is a block diagram illustrating the functional relationship of the major components of the stereoscopic fluoroscope apparatus.

Referring to FIG. 2, the x-ray tubes 2 and 3, the image intensifiers 4 and 5, and the video cameras 6 and 7 are all conventional components. The x-ray tubes irradiate the target 12 which absorbs the x-ray photons in a characteristic pattern. The absorption patterns are transmitted to the intensifiers and converted to fluorescent images which are scanned by the video cameras and converted to video signals of a standard format. The video signals are communicated to the display unit 8 where they are again converted to right and left images which are displayed on the video display devices.

In order to prevent a confusion of images, the x-ray tubes 2 and 3 are alternately cycled such that only one tube is active at a time. This cycling of the x-ray tubes are coordinated with the scan of the video cameras to prevent such effects as strobing. The x-ray source timer switch 11 may be adapted to directly switch the high voltage from a high voltage power supply 23 or, more likely, to switch low voltage signals which in turn control the high voltage signals. Preferably, the video cameras 6 and 7 are activated in unison with the associated x-ray tubes to prevent effects in the displays 9 and 10 from x-rays of one of the x-ray tubes leaking to the opposite image intensifier.

The illustrated video cameras 6 and 7 are connected through a video signal switching unit 25 to right and left video circuits 26. The unit 25 is fairly conventional in itself and includes video distribution amplifiers for selectively distributing the video signals to remote video monitors 27, right and left video recorders 28, and a graphics and text computer 29. The remote monitors 27 may be employed for training diagnosticians in fluoroscopic techniques or for consultation purposes. The video recorders 28 allow the recording of the fluoroscopic images for subsequent consultations with other physicians, comparison of conditions at various times during a course of treatment, or for training purposes. For stereoscopic viewing of the recorded images, it is necessary that the left and right images be synchronized. This may be accomplished by using specially designed multiple track video recording machines or by the synchronization of separate recording units for the left and right signals. The recorders could be synchronized by means of address tracks recorded on the separate video tapes which are compared to control the drive motors of the recording units. A microphone 30 may be connected more or less directly to the remote monitors 27 or may be connected to the video recorders for recording a commentary.

The computer 29 may be employed for digitizing and storing images received from the image intensifiers 4 and 5 through the cameras 6 and 7. Digital storing of the images may be done in some circumstances for computer enhancement of the images. Such techniques may be employed for computerized diagnosis or identification in conjuction with more conventional approaches. The provision of the computer 29 also provides for the use of very high capacity storage techniques such as laser discs when such technologies have been developed to the point that recordings can be made economically other than in a manufacturing situation. The connections of the video recorders 28 and computer 29 are bilateral such that these devices may serve as video sources of images to be displayed on the viewer unit 8. For example, simplified diagrams and texts such as catalogs of images may be displayed from the computer 29.

Figure 3:
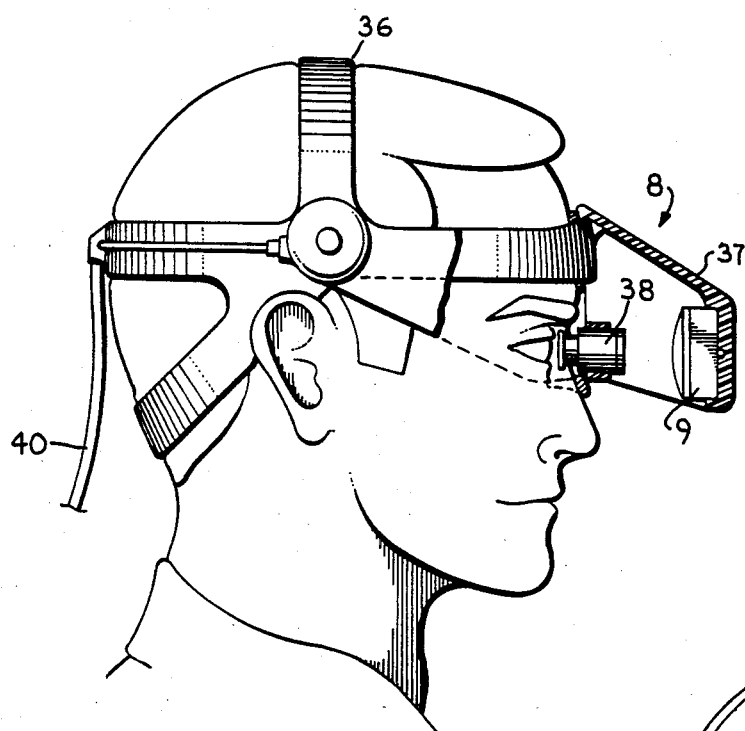
FIG. 3 is a side elevational view of a video stereoscopic viewer unit by which the fluoroscopic images are stereoscopically displayed, with a portion broken away to illustrate details of the viewer unit.
Figure 4:
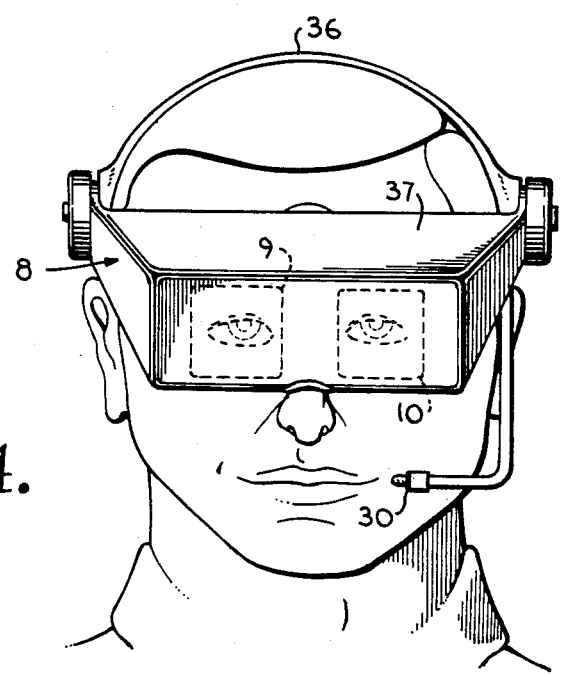
FIG. 4 is a front elevational view of the viewer unit.
Figure 5:
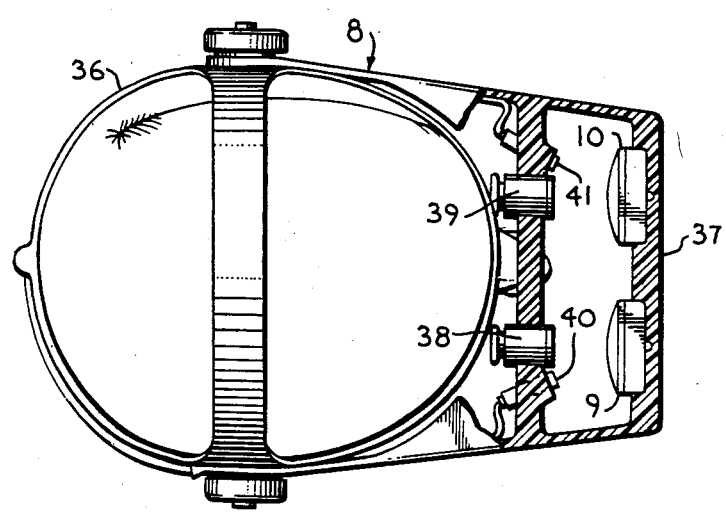
FIG. 5 is a top plan view of the viewer unit with a portion broken away to illustrate internal details.

FIGS. 3-5 illustrate an exemplary video stereoscopic viewer unit 8. The view unit 8 generally includes a viewer unit support harness or headband 36 to which is pivotally connected a visor 37 having the video displays 9 and 10 positioned therein. The harness 36 is preferably adjustable and is adapted for wearing on the head of a medical practitioner who is viewing the images generated by the x-ray tube. In addition to the video displays 9 and 10, the visor 37 provides a mounting for right and left viewer unit optical elements 38 and 39 which compensate for the close spacing between the video displays 9 and 10 and the practitioner's eyes.

The illustrated video display devices 9 and 10 are liquid crystal displays (LCD's). While high resolution LCD units, particularly high resolution color LCD units, are currently relatively expensive, and display images whose quality is inferior to cathode ray tube (CRT) units of the same size, the reduction in weight and size of the viewer unit 8 employing LCD devices justifies their expense. The prices of high resolution and contrast LCD's are expected to trend downward due to ongoing developments in LCD technologies and also because of the employment of such displays in computers and in consumer products such as pocket television receivers. Since the exposure of the practitioner's eyes to x-radiation with LCDs is substantially less than with CRTs, the display devices 9 and 10 can be mounted directly in line of sight of the practitioner. In contrast, it is generally desirable that CRT displays be viewed indirectly when viewed so close to avoid such radiation exposure. A video stereoscopic viewer unit which is suitable for use with the apparatus 1 and which employs CRT displays is described and illustrated in my copending application Ser. No. 616,385 entitled STEREOSCOPIC REMOTE VIEWING SYSTEM (now U.S. Pat. No. 4,559,555) which is incorporated herein by reference.

It is desirable to mount a major portion of the video circuitry which drives the displays 9 and 10 elsewhere than directly on the viewer unit 8 to keep the viewer unit as light as possible to avoid unnecessarily fatiguing the wearer of the unit. The video circuitry 26 (FIG. 2) is preferably mounted on a belt worn by the practitioner such that the video signals are conducted to the display devices 9 and 10 by means of viewer unit cables 40. The type of video circuitry required for such LCD displays would occur to one skilled in the video arts and is, therefore, not detailed here. Since LCD devices do not radiate their own light, they must be illuminated by a separate source. The LCD display devices 9 and 10 may be backlighted or, as illustrated, be illuminated reflectively by respective light sources 40 and 41 depending upon the type of LCD devices employed. The viewer unit 8 may also mount the microphone 30 by means of which a surgeon may provide a verbal commentary or discussion to accompany the fluoroscopic images.

It is to be understood that while certain forms of the present invention have been illustrated and described herein, it is not to be limited to the specific forms or arrangement of parts described and shown.

What is claimed and desired to be secured by Letters Patent is as follows:

1. A stereoscopic fluoroscope apparatus comprising:
   (a) a right x-ray source and a left x-ray source supported in spaced relation and controlled to irradiate a target of examination with x-rays;
   (b) a right image intensifier and a left image intensifier each supported in spaced relation to a respective x-ray source to form a fluorescent radiographic image wherein said target is irradiated by x-rays of the associated x-ray source;
   (c) a right video camera and a left video camera coupled respectively with the image intensifiers and converting the fluorescent images to video signals representing same;
   (d) a video stereoscopic display unit including right and left video display devices operatively connected respectively to said right and left cameras and positioned for stereoscopic viewing of said images of said target, said right and left video display devices being liquid crystal display devices; and
   (e) head support means having said stereoscopic display unit mounted thereon for supporting said display unit entirely by the head of a viewer of said display unit.

2. An apparatus as set forth in claim 1 including:
   (a) timer switch means connected to the x-ray sources to periodically and alternately activate said x-ray sources to irradiate said target.

3. An apparatus as set forth in claim 1 including:
   (a) video recorder means interconnected between said cameras and said display unit for recording said video signals representing said images of said target.

4. An apparatus as set forth in claim 1 including:
   (a) an extra video monitor interconnected between said cameras and said display unit for displaying images sensed by one of said cameras at a location remote from said display unit.

5. An apparatus as set forth in claim 1 including:
   (a) computer means interconnected between said cameras and said display unit for digitizing and storing said images and for displaying previously digitized and stored images on said display unit.

6. An apparatus as set forth in claim 1 wherein:
   (a) said video display devices are color video display devices; and
   (b) said computer means includes color graphics circuitry for color enhancing said images and for displaying the color enhanced images on said display unit.

7. An apparatus as set forth in claim 1 including:
   (a) video signal switching means interconnected between said cameras and said display unit and providing for the routing of said video signals from said cameras to external video signal utilization devices and the routing of external video signals to said display unit to display images represented by said external video signals on said display unit.

8. An apparatus as set forth in claim 1 including:
   (a) a substantially semicircular support arm supporting the x-ray sources and the image intensifiers and cameras in respective diametrically spaced relation.

9. An apparatus as set forth in claim 8 including:
   (a) a support base having said support arm movably connected thereto; and
   (b) motor means connected between said base and said arm for selective positioning of said x-ray sources and said image intensifiers and cameras in relation to said target.

10. A stereoscopic fluoroscope apparatus comprising:
    (a) a support base;
    (b) a substantially semicircular support arm movably connected to said base;
    (c) motor means connected between said base and said arm to selectively position said arm;
    (d) a right x-ray source and a left x-ray source positioned in spaced relation on said arm;
    (e) timer switch means connected to the x-ray sources to periodically and alternately activate said x-ray sources to irradiate a target of examination;
    (f) a right image intensifier and a left image intensifier positioned in spaced relation on said arm and diametrically across said arm respectively from said x-ray sources, the image intensifiers forming respective fluorescent images of said target as irradiated by the associated x-ray source;

(g) a right video camera and a left video camera coupled respectively to said image intensifiers and converting the fluorescent images to respective signals representing same;

(h) a video stereoscopic display unit including right and left video display devices operatively connected respectively to said right and left cameras and positioned for stereoscopic viewing of said images of said target, said right and left video display devices being liquid crystal display devices; and (i) head support means having said stereoscopic display unit mounted thereon for supporting said display unit entirely by the head of a viewer of said display unit.

11. An apparatus as set forth in claim 10 including:

(a) computer means interconnected between said cameras and said display unit for digitizing and storing said images and for displaying previously digitized and stored images on said display unit.

12. An apparatus as set forth in claim 10 including:

(a) an extra video monitor interconnected between said cameras and said display unit for displaying images sensed by one of said cameras at a location remote from said display unit.

13. A stereoscopic fluoroscope apparatus comprising:

(a) a support base;

(b) a substantially semicircular support arm movably connected to said base;

(c) motor means connected between said base and said arm to selectively position said arm;

(d) a right x-ray source and a left x-ray source positioned in spaced relation on said arm;

(e) timer switch means connected to the x-ray sources to periodically and alternately activate said x-ray sources to irradiate a target of examination;

(f) a right image intensifier and a left image intensifier positioned in spaced relation on said arm and diametrically across said arm respectively from said x-ray sources, the image intensifiers forming respective fluorescent images of said target as irradiated by the associated x-ray source;

(g) a right video camera and a left video camera coupled respectively to said image intensifiers and converting said fluorescent images to respective video signals representing same;

(h) a video stereoscopic display unit including right and left color video display devices operatively connected respectively to said right and left cameras and positioned for stereoscopic viewing of said images of said target, said right and left color video display devices being color liquid crystal display devices;

(i) computer means interconnected between said cameras and said display unit to digitize and store said images and to display previously digitized and stored images on said display unit;

(j) said computer means including color graphics circuitry to color enhance said images and to display the color enhanced images on said display unit; and (k) head support means having said stereoscopic display unit mounted thereon for supporting said display unit entirely by the head of a viewer of said display unit.

14. A stereoscopic fluoroscope apparatus comprising:

(a) a right x-ray source and a left x-ray source supported in spaced relation and controlled to irradiate a target of examination with x-rays;

(b) a right image intensifier and a left image intensifier each supported in spaced relation to a respective x-ray source to form a fluorescent radiographic image such that said target is irradiated by x-rays of the associated x-ray source;

(c) a right video camera and a left video camera coupled respectively with the image intensifiers and converting the fluorescent images to video signals representing same;

(d) a video stereoscopic display unit including right and left video display devices operatively connected respectively to said right and left cameras and positioned for stereoscopic viewing of said images of said target, said right and left video display devices being cathode ray tubes; and (e) head support means having said stereoscopic display unit mounted thereon for supporting said display unit entirely by the head of a viewer of said display unit.

15. A stereoscopic fluoroscope apparatus comprising:

(a) a support base;

(b) a substantially semicircular support arm movably connected to said base;

(c) motor means connected between said base and said arm to selectively position said arm;

(d) a right x-ray source and a left x-ray source positioned in spaced relation on said arm;

(e) timer switch means connected to the x-ray sources to periodically and alternately activate said x-ray sources to irradiate a target of examination;

(f) a right image intensifier and a left image intensifier positioned in spaced relation on said arm and diametrically across said arm respectively from said x-ray sources, the image intensifiers forming respective fluorescent images of said target as irradiated by the associated x-ray source;

(g) a right video camera and a left video camera coupled respectively to said image intensifiers and converting the fluorescent images to respective signals representing same;

(h) a video stereoscopic display unit including right and left video display devices operatively connected respectively to said right and left cameras and positioned for stereoscopic viewing of said images of said target, said right and left video display devices being cathode ray tubes; and (i) head support means having said stereoscopic display unit mounted thereon for supporting said display unit entirely by the head of a viewer of said display unit.

16. A stereoscopic fluoroscope apparatus comprising:

(a) a support base;

(b) a substantially semicircular support arm movably connected to said base;

(c) motor means connected between said base and said arm to selectively position said arm;

(d) a right x-ray source and a left x-ray source positioned in spaced relation on said arm;

(e) timer switch means connected to the x-ray sources to periodically and alternately activate said x-ray sources to irradiate a target of examination;

(f) a right image intensifier and a left image intensifier positioned in spaced relation on said arm and diametrically across said arm respectively from said x-ray sources, the image intensifiers forming respective fluorescent images of said target as irradiated by the associated x-ray source;

(g) a right video camera and a left video camera coupled respectively to said image intensifiers and converting said fluorescent images to respective video signals representing same;

(h) a video stereoscopic display unit including right and left color video display devices operatively connected respectively to said right and left cameras and positioned for stereoscopic viewing of said images of said target, said right and left color video display devices being color cathode ray tubes;

(i) computer means interconnected between said cameras and said display unit to digitize and store said images and to display previously digitized and stored images on said display unit;

(j) said computer means including color graphics circuitry to color enhance said images and to display the color enhanced images on said display unit; and (k) head support means having said stereoscopic display unit mounted thereon for supporting said display unit entirely by the head of a viewer of said display unit.

* * * * *